United States Patent [19]

Haber et al.

[11] Patent Number: 5,354,284
[45] Date of Patent: Oct. 11, 1994

[54] MULTIPLE INJECTION SYRINGE SYSTEM

[75] Inventors: Terry M. Haber, El Toro; Clark B. Foster, Laguna Niguel, both of Calif.

[73] Assignee: Habley Medical Technology Corporation, Laguna Hills, Calif.

[21] Appl. No.: 895,904

[22] Filed: Jun. 9, 1992

[51] Int. Cl.⁵ .............................................. A61M 5/00
[52] U.S. Cl. .................................... 604/191; 604/232
[58] Field of Search .............. 604/191, 218, 232, 415, 604/187, 181, 195, 197; 222/144.5, 389

[56] References Cited

U.S. PATENT DOCUMENTS

| | | | |
|---|---|---|---|
| 2,153,594 | 4/1939 | Saffir . | |
| 2,168,686 | 8/1939 | Saffir . | |
| 4,367,737 | 1/1983 | Kozam et al. . | |
| 4,549,674 | 10/1985 | Alticosalian | 222/48 |
| 4,610,666 | 9/1986 | Pizzino . | |
| 4,734,261 | 3/1988 | Koizumi et al. . | |
| 4,915,695 | 4/1990 | Koobs . | |
| 5,078,691 | 1/1992 | Hamacher | 604/191 |
| 5,137,528 | 8/1992 | Crose | 604/415 |
| 5,147,323 | 9/1992 | Haber et al. | 604/191 |
| 5,199,949 | 4/1993 | Haber et al. | 604/88 |

FOREIGN PATENT DOCUMENTS 79731 11/1919 Switzerland .
1055518 11/1983 U.S.S.R. .

Primary Examiner—C. Fred Rosenbaum
Assistant Examiner—V. Alexander
Attorney, Agent, or Firm—Hawes & Fischer

[57] ABSTRACT

A multiple injection syringe system having a cartridge carrier that is loaded with three pre-filled cartridges which are to be selectively accessed so that the contents of the cartridges can be delivered to a patient in a particular, predetermined order. The syringe system of the present invention has particular application to facilitating the SASH process, such that two of the cartridges are filled with saline and one with heparin. A double ended needle cannula is carried by a rotatable manifold. One end of the cannula projects outwardly from the manifold for administering an injection, while the opposite end projects inwardly to communicate with a selected cartridge within the carrier. The manifold is rotated around the cartridge carrier to each of three positions corresponding to three steps of the SASH process, whereby the cannula is correspondingly rotated from one cartridge to the next. Fluid from the selected cartridge is expulsed via the cannula by applying to said cartridge a hydraulic pressure that is generated by driving a piston through a fluid filled cylinder.

23 Claims, 5 Drawing Sheets

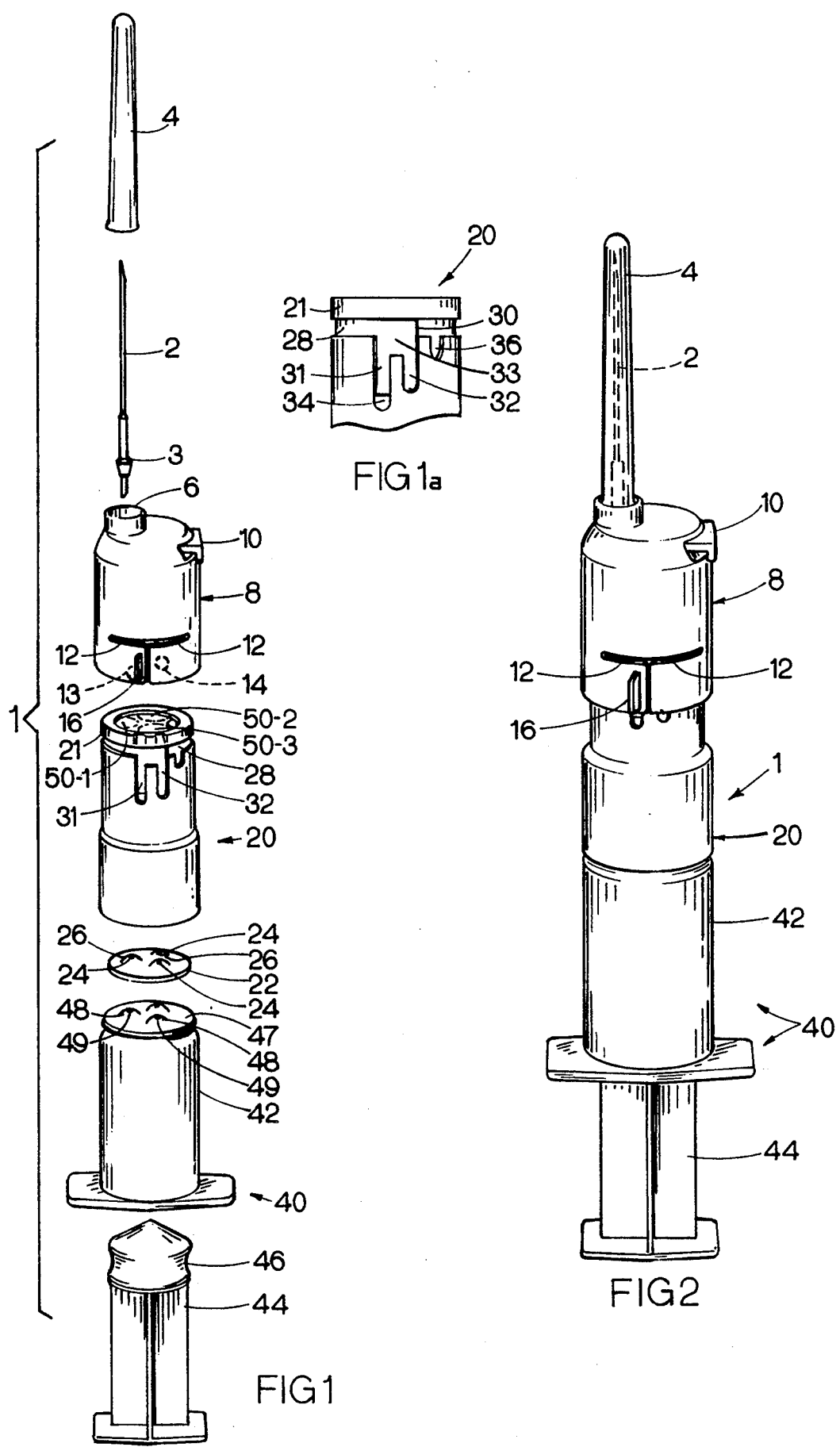

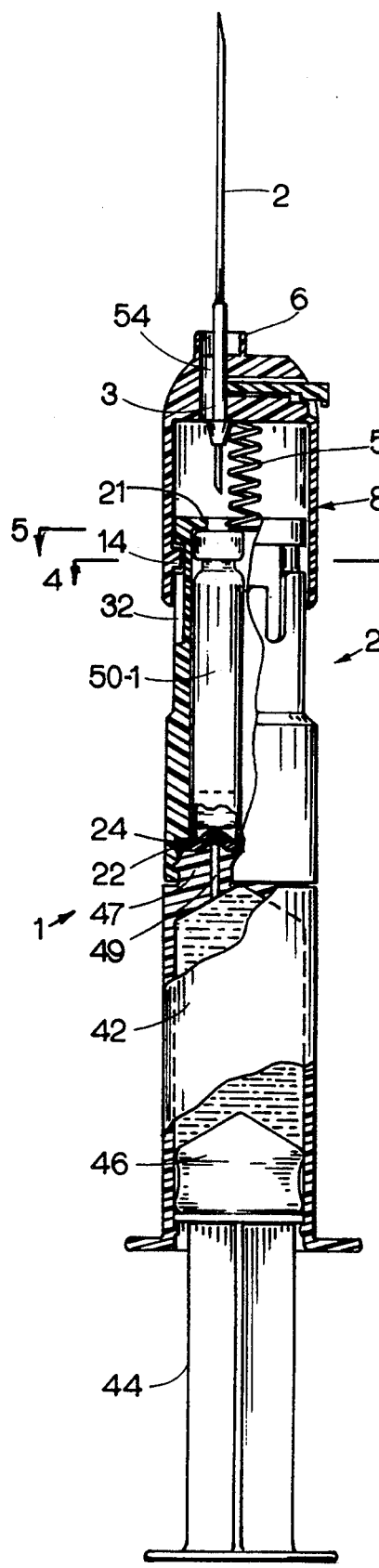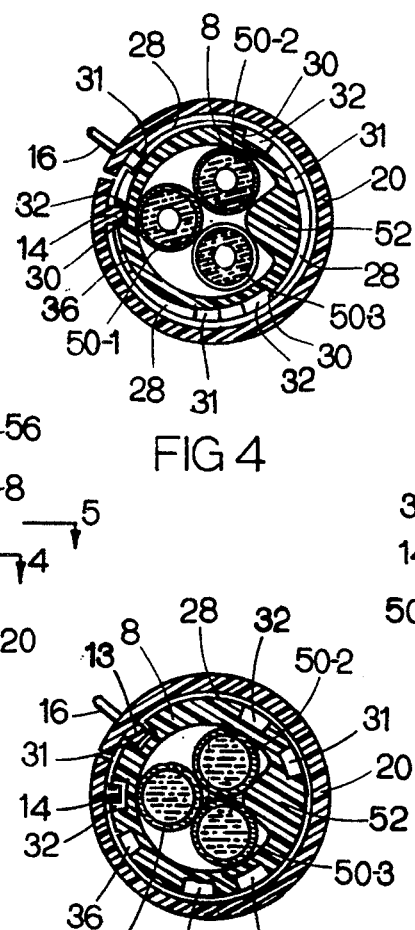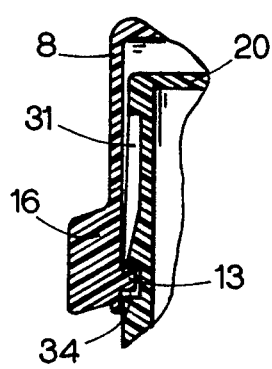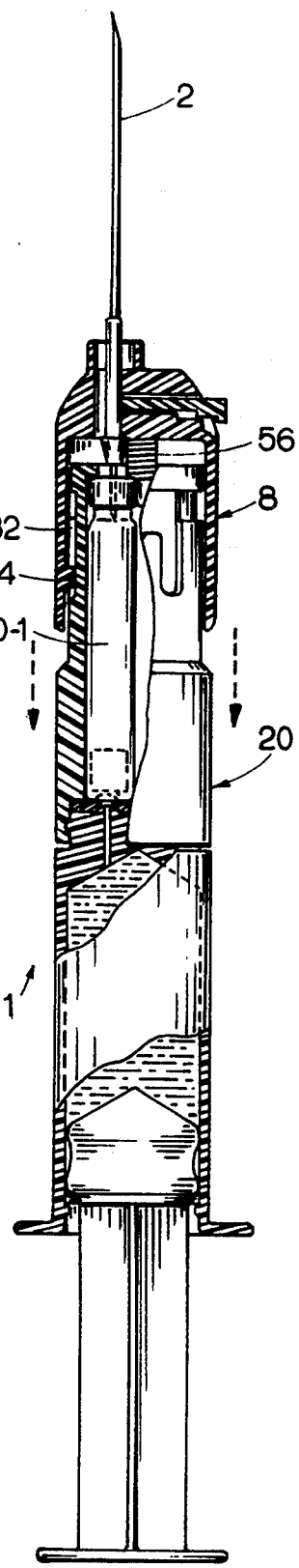
FIG 3  FIG 4  FIG 5  FIG 7  FIG 6

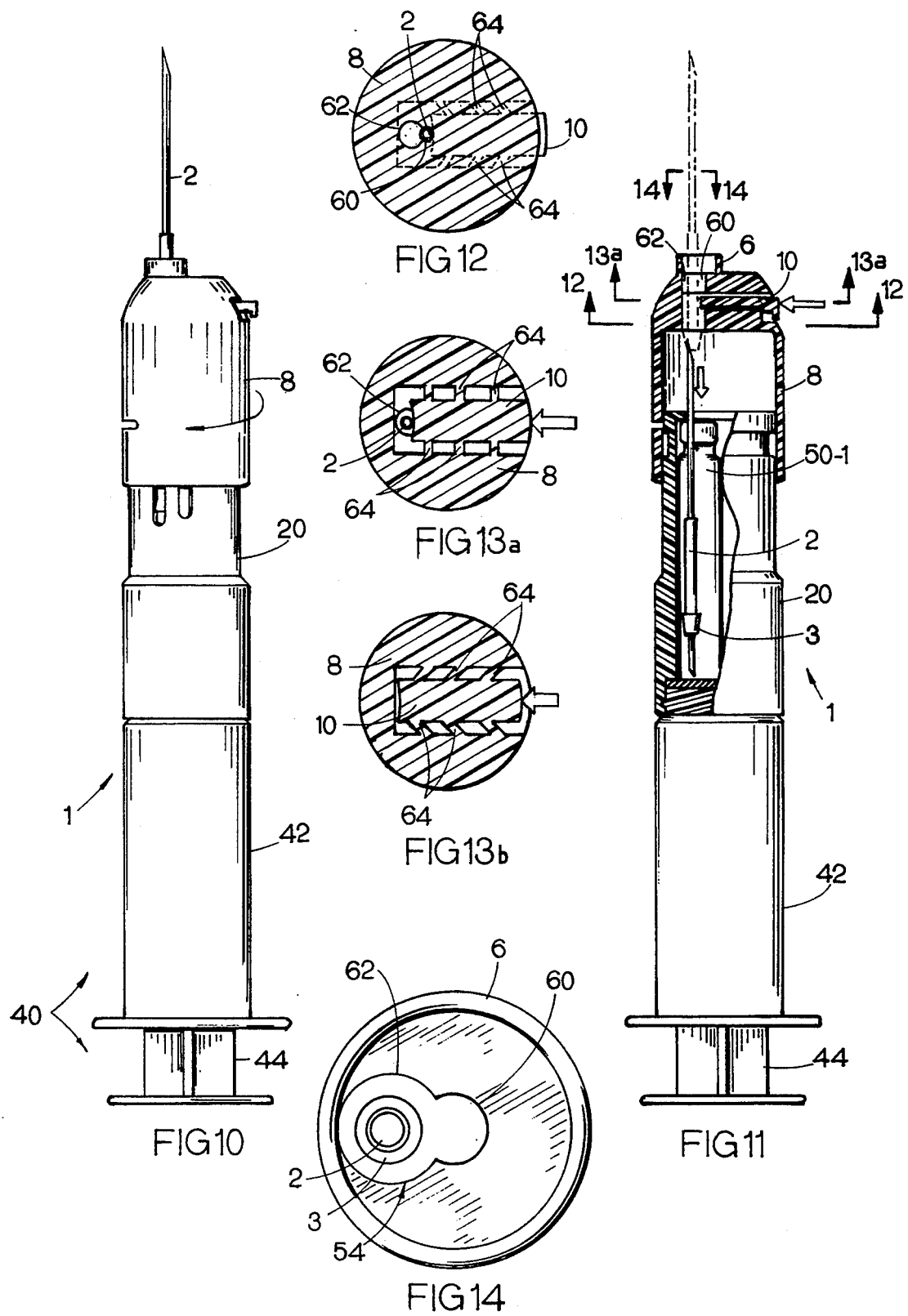

MULTIPLE INJECTION SYRINGE SYSTEM

BACKGROUND OF THE INVENTION

1. Field of the Invention

This invention relates to a multiple injection syringe system having a plurality of pre-filled fluid cartridges that are to be selectively accessed in a predetermined order to facilitate the SASH (Saline-Administration Medication-Saline-Heparin) process.

2. Prior Art

As will be known to health care workers, patients who are medicated or who are to receive certain intravenously administered drugs on a regular basis are commonly fit with an IV catheter. A dosage of saline is first delivered to the catheter from a hypodermic syringe. Next, a particular drug is administered to the patient, usually by means of another syringe. Then, another dosage of saline is applied to the catheter, via an additional syringe, to flush from the catheter any remnants of the previously administered drug. Lastly, heparin (or similar anti-coagulant) is applied to the patient to prevent clotting.

The foregoing steps are commonly known as the SASH (Saline-Administration Medication-Saline-Heparin) process. Unfortunately, the SASH process requires that health care workers have access to and handle several medication cartridges and the syringes by which to deliver the contents of such cartridges. Consequently, the administration of the drug according to the SASH process can be both time consuming and inefficient and will require the health care worker to be certain that the proper medication cartridges have been selected and delivered to the patient in a medically correct order.

It would be advantageous to eliminate the necessity for the health care worker to handle a variety of cartridges and syringes. It would also be desirable to make the SASH process more efficient by packaging the desired medication cartridges in a single syringe system by which to permit easy access to the cartridges in a particular, predetermined order. Accordingly, the possibility of selecting the wrong cartridge or administering the medication thereof at the wrong time can be minimized.

SUMMARY OF THE INVENTION

In general terms, a multiple injection syringe system is disclosed by which to facilitate the administration of a medication by means of the SASH (Saline-Administration Medication-Saline-Heparin) process. The syringe system includes a cartridge carrier which is loaded with three pre-filled cartridges. Two of the cartridges are filled with saline and the third cartridge is filled with heparin. The cartridge carrier has a network of channels, including a channel extending peripherally around the carrier and three pairs of channels communicating with and extending longitudinally from the peripheral channel. The pairs of channels are evenly spaced from one another around the cartridge carrier at positions corresponding to three of the steps of the SASH process. A ramp-shaped stop is located within the peripheral channel of the cartridge carrier at each of the positions corresponding to the aforementioned three steps of the SASH process.

A double ended hypodermic needle cannula is detachably retained by a rotatable manifold, such that a distal end of the cannula projects outwardly from the manifold to communicate with the patient's IV catheter while the proximal end of the cannula projects inwardly from the manifold. The cannula carrying manifold is to be successively rotated relative to the cartridge carrier to each of the positions therearound or corresponding to the aforementioned three steps of the SASH process. In the as-packaged configuration of syringe system, the rotatable manifold is spaced forwardly of the cartridge carrier, and the cannula is arranged in spaced, coaxial alignment above the first cartridge filled with saline, corresponding to the first step of the SASH process.

The rotatable, cannula carrying manifold includes an upper and a lower rotation control bump projecting radially inward thereof for receipt within the network of channels formed around the cartridge carrier. The upper rotation control bump rotates through the peripheral channel and rides up and over a ramp-shaped stop therein. The lower rotation control bump rotates around the circumference of the cartridge carrier for receipt within one of the pair of axial channels. With the upper rotation control bump located behind a stop and the lower rotation control bump located within an axial channel, the cannula carrying manifold is blocked from rotation in either a clockwise or a counterclockwise direction. At this point, the manifold may be moved rearwardly towards the cartridge carrier to correspondingly move the proximal end of the cannula into fluid communication with the first of the cartridges. Means are provided by which to releasably lock the cannula in fluid communication with said cartridge.

The syringe system also includes a cylinder that is filled with a fluid (e.g. water). The cylinder is connected to the cartridge carrier and communicates fluidically therewith via a fluid path. A piston stem, to which a piston is attached, is moved through the cylinder to drive the piston therethrough. Accordingly, fluid is supplied from the cylinder to the cartridge carrier through the fluid path therebetween to generate a hydraulic pressure which is sufficient to cause the saline to be expulsed from the first cartridge via the cannula.

After the first cartridge has been emptied, the cannula carrying manifold is moved away from the cartridge carrier, whereby the cannula is unlocked and removed from said cartridge. A finger ledge is raised to lift the lower position control bump out of its axial slot and thereby permit the manifold to be rotated around the cartridge carrier to the second position corresponding to another step of the SASH process. The needle cannula is also rotated so as to be in spaced, coaxial alignment above a second of the cartridges within the cartridge carrier. Fluid is expulsed from the second cartridge in the same manner as previously described when referring to the first cartridge. After the second cartridge has been emptied, the cannula carrying manifold is rotated around the cartridge carrier to the third position corresponding to the last step of the SASH process. Likewise, the needle cannula is also rotated so as to be in spaced, coaxial alignment above the third of the three cartridges. Fluid is expulsed from the third cartridge, in the manner previously described, so as to complete the SASH process.

A transfer plate is interfaced with the cannula carrying manifold and adapted to slide laterally therethrough. That is, the transfer plate is adapted to engage the needle cannula and push said cannula into a needle release hole formed in the manifold. Accordingly, the needle is free to drop through the needle release hole for receipt within the cartridge carrier thereunder. The cannula is thereby safely shielded and rendered inaccessible so that the syringe system of the present invention may be handled and/or safely discarded without fear of an accidental needle stick.

BRIEF DESCRIPTION OF THE DRAWINGS

FIG. 1 is an exploded view of the multiple injection syringe system which forms the present invention;

FIG. 1a is a detailed enlargement of a portion of a cartridge carrier which forms the syringe system of FIG. 1 and into which three fluid filled cartridges are loaded;

FIG. 2 shows the syringe system of FIG. 1 in the assembled, as-packaged configuration;

FIG. 3 is a partial cross-section of the syringe system of FIG. 2;

FIG. 4 is a cross-section taken along lines 4—4 of FIG. 3;

FIG. 5 is a cross-section taken along lines 5—5 of FIG. 3;

FIG. 6 is a partial cross-section of the syringe system in the activated configuration with a double ended needle cannula retained in fluid communication with a first fluid filled cartridge;

FIG. 7 is a detailed enlargement to illustrate means for releasably retaining the syringe system of FIG. 6 in the activated configuration;

FIGS. 9 and 10 illustrate steps for rotating the manifold so that the cannula carried thereby can be positioned to communicate with another fluid filled cartridge;

FIG. 11 shows the needle cannula after it has been released from the rotatable manifold and received within the cartridge carrier;

FIG. 12 is a cross-section taken along lines 12—12 of FIG. 11 showing the cannula being released from the rotatable manifold;

FIG. 13a is a cross-section taken along lines 13a—13a of FIG. 11 also showing the cannula being released from the rotatable manifold;

FIG. 13b is a cross-section taken along lines 13a—13a of FIG. 11 after the needle cannula has been released from the rotatable manifold;

FIG. 14 is an end view taken along lines 14—14 of FIG. 11 after the cannula has been released from the manifold;

DESCRIPTION OF THE PREFERRED EMBODIMENT

Figure 8:
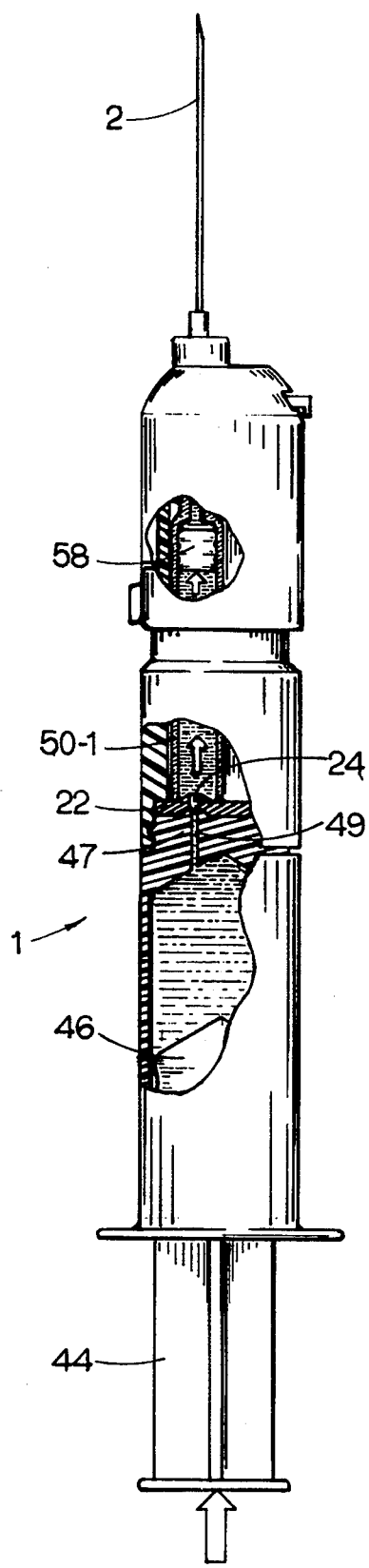
FIG. 8 illustrates the step for expulsing the contents of the first fluid filled cartridge via the needle cannula that is carried by a rotatable manifold.

The multiple injection syringe system 1 of the present invention to facilitate the administration of a medication according to the SASH (Saline-Administration Medication-Saline-Heparin) is best described while referring to the drawings, where FIG. 1 shows an exploded view of the syringe system. The syringe system 1 includes a double ended needle cannula 2 having opposing proximal and distal ends and an integral needle hub 3 formed (e.g. molded) adjacent the proximal end thereof. A removable needle cover 4 is provided to shield the distal end of cannula 2 and thereby prevent the loss of sterility and an accidental needle stick.

The distal end of needle cannula 2 projects outwardly through a collar 6 of a hollow, cylindrical, rotatable manifold 8. The needle hub 3 of cannula 2 is retained by manifold 8 in the outwardly extending position so that fluid can be expulsed from syringe 1 to an IV catheter via said cannula. However, and as will be described in greater detail when referring to FIG. 11, a slidable transfer plate 10 is movable laterally relative to manifold 8 to correspondingly release the cannula 2 from the manifold and thereby permit said cannula to be received completely within and safely shielded by the syringe system 1. A side of manifold 8 is provided with a pair of slots 12. Each slot may be of any suitable configuration so as to provide manifold 8 with a spring-like resiliency or flexibility necessary to permit the bottom of said manifold to expand and thereby receive therewithin a soon to be described cartridge carrier 20. A lower rotation control bump 13 and an upper rotation control bump 14 project radially inward from manifold 8. The rotation control bumps 13 and 14 are positioned relative to one another so that, in the assembled configuration (of FIG. 2), bumps 13 and 14 are received within respective channels formed in the cartridge carrier 20 to permit manifold 8 to be successively rotated to and releasably locked at each of three different positions around said carrier (corresponding to the three steps of the SASH process) for a purpose that will be explained in greater detail hereinafter. A finger ledge 16 projects radially outward from manifold 8. As will be explained when referring to FIG. 9, the finger ledge 16 may be lifted by a health care worker to release the manifold 8 from one position for rotation to a successive position around carrier 20.

Cartridge carrier 20 is a hollow, elongated cylindrical member having open proximal and distal ends. As is best shown in FIGS. 3, 4 and 5, three pre-filled cartridges 50-1, 50-2 and 50-3 are loaded into the cartridge carrier 20 through the open proximal end thereof during the assembly of syringe system 1. The fluid filled cartridges that are loaded into the carrier 20 include two cartridges 50-1 and 50-2 containing saline solution and one cartridge 50-3 containing heparin. It may be appreciated that the two saline and one heparin filled cartridges represent three of the drugs that are common to the SASH process. A peripheral lip 21 extends around the distal end of the carrier 20 to engage and retain the aforementioned fluid filled cartridges 50-1, 50-2 and 50-3 therewithin. After the carrier 20 has been loaded with the three cartridges 50-1, 50-2 and 50-3, the proximal end thereof is closed with a suitable seal 22 to prevent an inadvertent removal or reversal of the order of said cartridges. The seal 22 is provided with three fluid passages 24 which extend through raised dimples 26. The purpose of passages 24 will soon be explained. However, the raised dimples of seal 26 act as locators to properly align the three cartridges 50-1, 50-2 and 50-3 within cartridge carrier 20.

Referring concurrently to FIGS. 1 and 1a, the cartridge carrier 20 is provided with a network of channels which receive the lower and upper rotation control bumps 13 and 14 of rotatable manifold 8 to permit said manifold to be successively rotated to and releasably retained at each of the three positions around the carrier. More particularly, a first peripheral channel 28 extends continuously and circumferentially around the rotatable manifold 8 immediately below the lip 21 thereof. A total of three evenly spaced, ramp-shaped stops 30 (only one being shown) are formed within the peripheral channel 28, one stop being located at each of the three positions around cartridge carrier 20 to which manifold 8 will be successively rotated during the steps of the SASH process. A total of three pairs of axially extending channels 31 and 32 (only one pair being shown) communicate with peripheral channel 28 and project longitudinally and downwardly therefrom. One pair of channels 31 and 32 is located at each of the three positions around cartridge carrier 20 to which manifold 8 will be successively rotated during the steps of the SASH process. One of the axial channels 31 is longer than the other channel 32. A depression 34 is formed at the lower-most end of the relatively long axial channel 34 for a purpose that will be described when referring to FIG. 7. Each of the axial channels 31 and 32 communicates with one another by a bridge 33 extending therebetween. A single needle release detent 36 communicates with peripheral channel 28 and projects longitudinally and downwardly therefrom. Needle release detent 36 is located just past the third of the positions around cartridge carrier 20 to which manifold 8 will be rotated to complete the last step of the SASH process.

A syringe assembly 40 including a hollow cylinder 42 and a piston stem 44, to which a piston 46 is attached, is connected to cartridge carrier 20 so as to be in fluid communication therewith. That is, the distal end of hollow cylinder 42 is sealed by a disk-like flange 47. With syringe system 1 in the assembled, as-packaged configuration (best shown in FIG. 3), the flange 47 of cylinder 42 is snap-fit within a corresponding recess formed around the inner perhipery of cartridge carrier 20 and located immediately behind seal 22, so that the cylinder 24 of syringe assembly 40 may be connected to said carrier 20. Flange 47 is provided with three raised dimples 48, which correspond in shape and location to the raised dimples 26 of seal 22, so that dimples 48 will be received within and mated against the dimples of said seal 22 when the syringe system 1 is in the assembled, as-packaged configuration (also best shown in FIG. 3). Fluid passages 49 are formed through the dimples 48 of flange 47 so that three fluid channels are created between the syringe cylinder 42 and cartridge carrier 20 via the respective fluid paths 24 and 49 of dimples 26 and 48. Hence, and as will soon be explained, a non-compressible fluid (e.g. water or the like) may be expulsed from cylinder 42 to cartridge carrier 20 when the piston 46 is driven by piston stem 44 through said cylinder.

FIG. 2 of the drawings shows the multiple injection syringe system 1 of FIG. 1 in the assembled, as-packaged configuration. In such as-packaged configuration, the needle cannula 2 is retained by rotatable manifold 8 in the axially extended position with needle cover 4 surrounding and shielding the distal end of said cannula. Moreover, the bottom of manifold 8 is expanded at the slots 12 thereof to accommodate cartridge carrier 20, whereby the lower and upper rotation control bumps (designated 13 and 14 in FIG. 1) are received within and movable through the network of channels of carrier 20 so that manifold 8 can be successively rotated to and releasably engaged at three positions around said carrier corresponding to three steps of the SASH process. During assembly of the syringe system 1, the cylinder 42 of syringe assembly 40 is filled with fluid (e.g. water) and connected (i.e. snap-fit) to carrier 20 so as to communicate fluidically therewith. Piston stem 44 projects outwardly from cylinder 24 for driving the associated piston therethrough.

A cross-section of the multiple injection syringe system 1 in the assembled, as-packaged configuration of FIG. 2 is shown in FIG. 3 of the drawings. Although only a single fluid filled cartridge 50-1 is illustrated within cartridge carrier 20, it is to be understood, by referring to FIGS. 4 and 5, that a total of three conventional, pre-filled cartridges 50-1, 50-2 and 50-3 are loaded into carrier 20 during assembly of the system 1 to be selectively accessed during a series of steps corresponding to three of the steps of the SASH process. That is to say, first and second cartridges 50-1 and 50-2 are filled with saline and the third cartridge 50-3 is filled with Heparin. As is best shown in FIGS. 4 and 5, the cartridges 50-1, 50-2 and 50-3 are loaded into cartridge carrier 20 during assembly so as to be uniformly aligned with one another at an angle of 120 degrees. To preserve the desired alignment of the cartridges and to prevent any displacement thereof during handling of the system, a longitudinally extending rib 52 projects radially inward from carrier 20 to engage said cartridges.

In FIG. 3, the needle cannula 2 is shown with the hub 3 thereof being received within and retained at an orifice 54 formed through the rotatable manifold 8. Details of orifice 54 by which to either retain the cannula 2 for administering an injection or to release the cannula to permit disposal thereof will be provided when referring hereinafter to FIG. 14. However, in the as-packaged configuration of FIG. 3, the distal end of the cannula 2 projects axially and outwardly from the collar 6 of manifold 8, while the proximal end projects into said manifold to lie in spaced, coaxial alignment with the first cartridge 50-1 that is filled with saline. To maintain the spaced, coaxial alignment between cannula 2 and the first cartridge 50-1, a compression spring 56, or the like, extends between manifold 8 and the tops of each of the cartridges 50-1, 50-2 and 50-3, whereby to bias the manifold 8 forward of and away from the cartridge carrier 20. Spring 56 may, if desired, be molded as an integral part of manifold 8.

Referring concurrently to FIGS. 3–5, the upper rotation control bump 14 is shown projecting inwardly from rotatable manifold 8 for receipt against ramp-like stop 30 within the peripheral channel 28 of cartridge 20. As was previously described when referring to FIG. 1a, a stop 30 is located within peripheral channel 28 at each of the three positions of carrier 20 corresponding to a respective step of the SASH process. The stops 30 are ramped so as to permit both a clockwise rotation of upper rotation control bump 14 through channel 28 and over stop 30 and a corresponding clockwise rotation of the cannula carrying manifold 8 relative to cartridge carrier 20, but block a rotation of said bump 14 through channel 28 and manifold 8 around carrier 20 in the opposite, counter-clockwise direction. As will soon be described, the rotation control features provided by the interaction of upper bump 14 with the stops 30 of peripheral channel 28 assures that the cartridges 50-1, 50-2 and 50-3 of cartridge carrier 20 can be accessed only in a predetermined order corresponding to saline-saline-heparin steps of the SASH process.

Continuing to refer to FIGS. 3–5, the lower rotation control bump 13 is shown projecting inwardly from rotatable manifold 8 for receipt within the longer channel 31 of a pair of axial channels 31 and 32 of cartridge carrier 20. As previously disclosed when referring to FIG. 1a, a pair of axially extending channels 31 and 32 communicates with peripheral channel 28 at each of three successive positions around carrier 20 corresponding to respective steps of the SASH process. As will soon be described, the lower and upper rotation control bumps 13 and 14 are adapted to ride longitudinally through respective axial channels 31 and 32. However, in the as-packaged configuration of FIGS. 3–5, the receipt of lower rotation control bump 13 within axial channel 31 prevents both a clockwise rotation of said control bump and a clockwise rotation of the cannula carrying manifold 8 relative to cartridge carrier 20. Hence, it may be appreciated that the receipt of lower and upper bumps 13 and 14 by channels 31 and 32 prevents a rotation of the cannula carrying manifold 8 in both the clockwise and counter-clockwise directions relative to carrier 20 to thereby releasably retain said manifold 8 at a first of the three positions around carrier 20 corresponding to a first step of the SASH process. Accordingly, the needle cannula 2 carried by rotatable manifold 8 is locked at such first position in spaced coaxial alignment with the first saline filled cartridge 50-1.

Referring briefly once again to FIG. 3 where syringe system 1 is shown in the assembled, as-packaged configuration, the syringe cylinder 42 is pre-filled with a suitable non-compressible fluid (e.g. water) and connected (i.e. snap-fit) at the disk-like flange 47 thereof to the cartridge carrier 20. Piston stem 44 projects outwardly from the cylinder 42 so as to be adapted to drive associated piston 46 axially and distally through said cylinder and thereby expulse fluid through a path established from cylinder 42 to the first cartridge 50-1 via a fluid passage 49 of flange 47 and a fluid passage 24 of seal 22.

Referring now to FIG. 6 of the drawings, the multiple injection syringe system 1 is shown in the activated condition. More particularly, when it is desirable to initiate the SASH process, the distal end of the needle cannula 2 is interfaced with a conventional IV catheter (not shown). In order to infuse the catheter with saline, and thereby complete the first step of the SASH process, a health care worker merely grasps the cannula carrying manifold 8 and applies an axial pulling force thereto (in the direction indicated by the reference arrows). Hence, the compression spring 56 between manifold 8 and the cartridge carrier 20 is compressed, whereby manifold 8 is moved rearwardly and towards said carrier 20. Accordingly, the proximal end of needle cannula 2 will be correspondingly moved towards cartridge carrier 20 to penetrate the seal of first cartridge 50-1 and thereby communicate with the saline contents thereof.

With the movement of manifold 8 towards cartridge carrier 20, the radially inward projecting lower and upper rotation control bumps 13 and 14 of manifold 8 are, likewise, moved longitudinally and downwardly through the respective axial channels 31 and 32 which form the pair of channels located at the first of three successive positions around carrier 20 corresponding to the first step of the SASH process. As is best shown in FIG. 7, the lower rotation control bump 13 rides through the relatively longer axial channel 31 until it is received at the depression 34 thereof. With bump 13 received in depression 34, the cannula carrying manifold 8 will be detachably locked in the position shown in FIG. 6, with the cannula 2 retained in fluid communication with saline filled cartridge 50-1.

In FIG. 8 of the drawings, fluid is expulsed from the cylinder 42 for driving the piston 58 of cartridge 50-1 through said cartridge so that saline can be delivered to the patient's IV catheter to complete the first step of the SASH process. More particularly, the piston stem 44 is pushed axially (in the direction of the reference arrow) to correspondingly advance the associated piston 46 distally through the cylinder 42. The fluid within cylinder 42 is forced through a closed fluid path including fluid passage 49 of flange 47 and fluid passage 24 of seal 22. The resulting pressure generated by the fluid in the aforementioned fluid path is sufficient to drive piston 58 through its cartridge 50-1 so as to expulse the saline therefrom via needle cannula 2. It may be noted that no piston stem insert is required for piston 58, and piston stem 44 and piston 58 are hydraulically, rather than mechanically, interfaced with one another. Moreover, the piston 46 is moved partly through cylinder 42 in order that sufficient fluid is expulsed therefrom to drive piston 58 through its cartridge 50-1. However, it is desirable that there be enough fluid remaining within cylinder 42 to generate the hydraulic pressure necessary to also drive the respective pistons of cartridges 50-2 and 50-3 during subsequent steps of the SASH process.

At this point in the SASH process, the health care worker typically administers a medication according to the particular needs of the patient. Such medication is injected into the patient's IV catheter by means of a separate syringe. This step and means for administering the medication during the second step of the SASH process form no part of the present invention.

During the third step of the sash process, an additional supply of saline is commonly delivered to the patient's IV catheter to flush any remnant of the medication that was administered to the patient during the preceeding second step. Thus, and referring concurrently to FIGS. 4–9 of the drawings, it is necessary to relocate needle cannula 2 so as to position said cannula to communicate with the second of the cartridges 50-2 that is filled with saline. The foregoing is accomplished by rotating the cannula carrying manifold 8 in a clockwise direction to a second of the three positions around cartridge carrier 20 which corresponds to the third step of the SASH process.

As previously described when referring to FIGS. 6 and 7, the rotatable cannula carrying manifold 8 is releasably retained at the first position around cartridge carrier 20 with needle cannula 2 locked in fluid communication with the first cartridge 50-1. To detach cannula 2 from cartridge 50-1 and rotate manifold 8 in a clockwise direction relative to carrier 20 so that the cannula is aligned to communicate with the second cartridge 50-2, the health care worker first lifts or raises the finger ledge 16 of said manifold (best illustrated in FIG. 9). Hence, the lower rotation control bump 13 is moved out of the depression 34 at the lower-most end of axial channel 31. The potential energy stored within compression spring 56 returns said spring towards the relaxed condition, whereby manifold 8 is forced upwardly and away from cartridge carrier 20, and the lower and upper rotation control bumps 13 and 14 are caused to ride upwardly and longitudinally through their respective axial channels 31 and 32. Accordingly, the proximal end of cannula 2 is pulled out of and spaced above cartridge 50-1.

Figure 9:
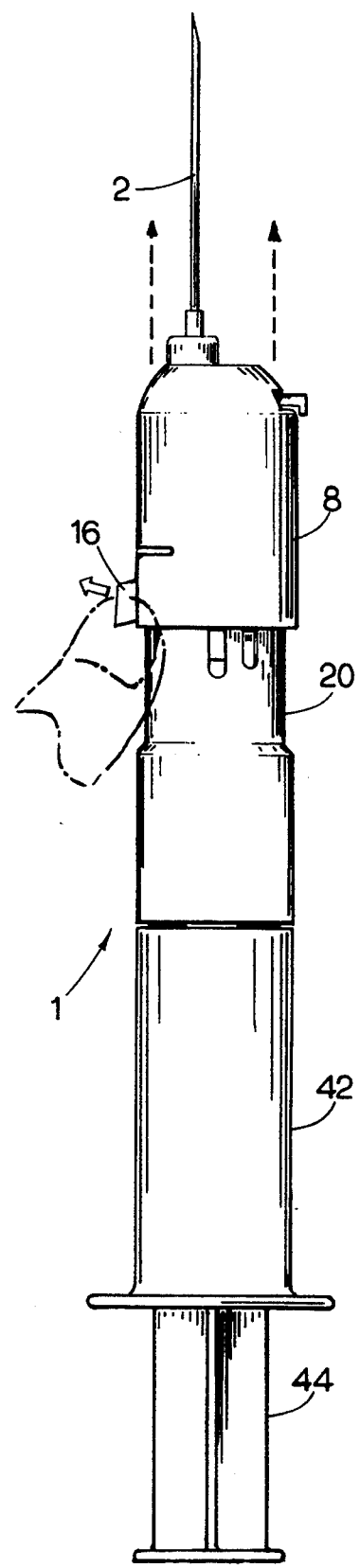

With the finger ledge 16 held in the raised position of FIG. 9, the health care worker next rotates the cannula carrying manifold 8 in a clockwise direction around the cartridge carrier 20 (best illustrated in FIG. 10). That is to say, by lifting the finger ledge 16, the lower rotation control bump 13 is lifted out of its axial channel 31 so as to permit said bump 13 to rotate, with manifold 8, circumferentially around carrier 20. Likewise, the upper rotation control bump 14 rotates with manifold 8 through its peripheral channel 28. The health care worker then releases the finger ledge 16 but continues to rotate manifold 8 around cartridge carrier 20 until the rotatable manifold 8 reaches the second of the three positions around carrier 20 corresponding to the third step of the SASH process. At such second position, the lower rotation control bump 13 is rotated into an axial channel 31 from a second of the pair of channels 31 and 32, whereby to prevent any further rotation of the cannula carrying manifold 8 in the clockwise direction. Similarly, the upper rotation control bump 14 is rotated through peripheral channel 28, so as to slide up and over a ramp-like stop 30, and thereby block any rotation of the manifold 8 in the counter-clockwise direction. Thus, cannula carrying manifold 8 is releasably retained at the second of the three positions around cartridge carrier 20 with needle cannula 2 located in spaced, coaxial alignment above the second of the cartridges 50-2 that is filled with saline (corrsponding to the third step of the SASH process).

The manner in which the cannula 2 is moved into fluid communication with cartridge 50-2 and the method by which to expulse the fluid (i.e. saline) contents thereof is similar to that described when referring to FIGS. 6-8. Briefly, however, and referring once again to FIGS. 6-8, with the cannula carrying manifold 8 is moved toward cartridge carrier 20, and the needle cannula 2 is locked in fluid communication with the second cartridge 50-2. The piston stem 44 is then advanced further into the cylinder 42, whereby to drive piston 46 through said cylinder 42. The hydraulic pressure generated by forcing piston 46 through cylinder 42 is sufficient to cause the piston associated with the second cartridge 50-2 to be driven through said cartridge, whereby to expulse the fluid therefrom via cannula 2. When the second cartridge 50-2 has been emptied of fluid, the needle cannula 2 is detached from the second cartridge, and the cannula carrying manifold 8 is rotated to a third position around the cartridge carrier 20 corresponding to the last step of the SASH process. Fluid (i.e. heparin) is expulsed from the third cartridge 50-3 in the same manner that fluid was expulsed from the first and second cartridges 50-1 and 50-2 during the first and third steps of the SASH process.

At the conclusion of the SASH process, after each of the cartridges 50-1, 50-2 and 50-3 has been selectively accessed in the particular order according to the SASH process, the needle cannula 2 can be removed from manifold 8 so as to be safely shielded and received within the cartridge carrier 20, whereby syringe system 1 can be safely handled and discarded while avoiding an accidental needle stick. More particularly, the finger ledge 16 is lifted and the cannula carrying manifold 8 is again rotated relative to cartridge carrier 20, whereby the lower rotation control bump 13 is automatically advanced into receipt by the needle release detent 36 (at FIGS. 1 and 1a) of carrier 20. Needle release detent 36 is located on carrier 20 beyond the position thereof corresponding to the last step of the SASH process at which the third cartridge 50-3 was accessed. With lower rotation control bump 13 in needle release detent 36, the needle cannula 2 will be positioned above an empty space of the cartridge carrier 20 where none of the now empty cartridges 50-1, 50-2 or 50-3 is located (see FIGS. 4 and 5). Accordingly, space is available in carrier 20 within which to receive the cannula 2 when said cannula is released from the needle orifice 54 (of FIG. 3) of cannula carrying manifold 8.

Referring concurrently to FIGS. 11-14 of the drawings, the needle orifice 54 which is formed through manifold 8 is shown having a keyhole configuration comprising a relatively small diameter needle retaining hole 60 in which to receive and retain the hub 3 of cannula 2 and an adjacent, larger diameter needle release hole 62, the diameter of which is larger than the corresponding diameter of the cannula hub. In the as-packaged configuration (of FIG. 3), cannula 2 is retained in an axially extending position within needle retaining hole 60 so as to be capable of injecting the contents of cartridges 50-1, 50-2 and 50-3 during steps of the SASH process. Also in the as-packaged configuration, the transfer plate 10 is located adjacent needle retaining hole 60 at the side of cannula 2 (best illustrated in FIG. 12). Tranfer plate 10 is attached to cannula carrying manifold 8 by means of a series of pivotal, over-center fingers or hinges 64. Hinges 64 are of flexible construction to permit transfer plate 10 to slide laterally through manifold 8. Accordingly, by applying a radially directed force to transfer plate 10 (in the direction of the reference arrow of FIG. 13a), said transfer plate 10 will move laterally at hinges 64 into contact with the needle cannula 2 at the needle retaining hole 60. The continued lateral displacement of transfer plate 10 will push cannula 2 out of needle retaining hole 60 and into the adjacent needle release hole 62. Inasmuch as the diameter of needle release hole 62 is larger than the diameter of needle hub 3, a displacement of the cannula 2 into needle release hole 62 will cause said cannula to fall, under the influence of gravity, through needle release hole 62 (best illustrated in FIG. 14) and into an empty space of the cartridge carrier 20. Eventually, tranfer plate 10 will be moved completely across the needle orifice 54 so as to cover both needle retaining hole 60 and needle release hole 62. Hence, access to the cannula 2 within cartridge carrier 20 is blocked by the extension of transfer plate 10 completely across needle orifice 54. With cannula 2 shielded by and rendered irretrievable within cartridge carrier 20 (best shown in FIG. 11), the syringe system 1 may be safely handled and/or discarded, as previously indicated.

Figure 15:
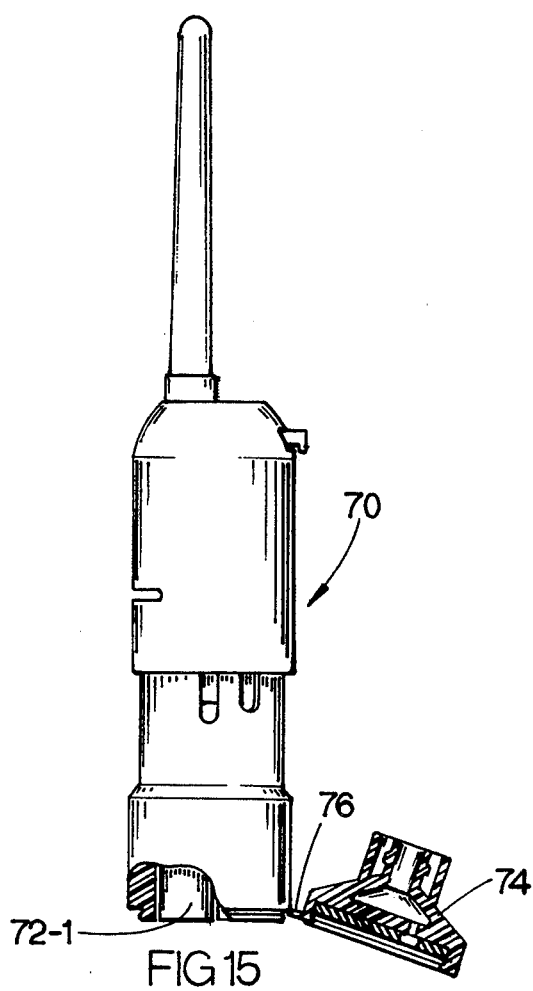
FIGS. 15 and 16 show a first alternate embodiment of the present invention.
Figure 16:
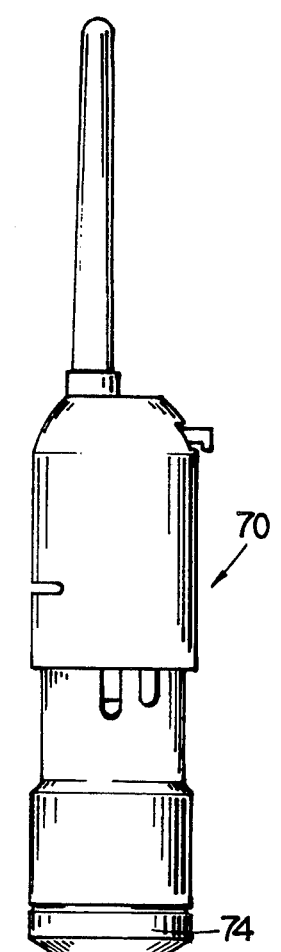

FIGS. 15 and 16 of the drawings illustrate a first alternate embodiment of the present invention. With the multiple injection syringe system 1 of FIGS. 1-14, fluid filled cylinder 42 of syringe 40 was connected (i.e. snap-fit) to cartridge carrier 20 to form a one-piece construction. However, the multiple injection syringe system 70 of FIGS. 15 and 16 includes a syringe adapter 74 to which a conventional syringe 77 may be removably mated. More particularly, syringe adapter 74 is connected to syringe system 70 by means of a hinge 76. Thus, syringe adapter 74 may be rotated to an open position (as shown in FIG. 15) at which to insert the pre-filled cartridges (e.g. 72-1). Syringe adapter 74 may then be rotated to a closed configuration (best shown in FIG. 16) so that the cylinder 78 of syringe 77 may be screwed into mating engagement therewith. Syringe 77 is of conventional design and includes the cylinder 78 and a piston stem 79 for driving a piston (not shown) therethrough so as to generate a hydraulic force for the purpose previously disclosed when referring to FIGS.

1-14. However, by virtue of the syringe system 70 of FIGS. 15 and 16, syringe 77 and syringe system 70 may be packaged, stored and discarded separately from one another to facilitate handling and transport.

Figure 17:
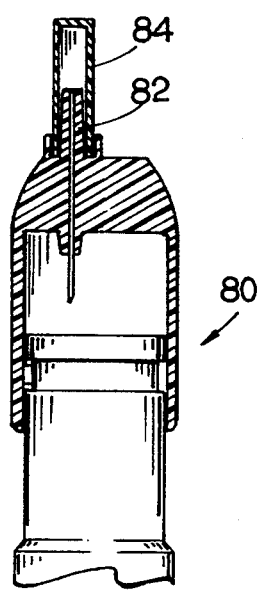
FIG. 17 shows a second alternate embodiment of the present invention.

FIG. 17 of the drawings shows a multiple injection syringe system 80 according to a second alternate embodiment of the present invention. More particularly, instead of retaining a needle cannula within the needle orifice 54 of FIGS. 1-16, it is within the scope of this invention to manufacture a syringe system 80, as previously disclosed, having a conventional luer lock fitting 82 at which to engage and retain said cannula. Luer lock 82 is provided with the usual removable cover 84. It is therefore to be understood that the needle cannula may either have a hub (designated 3 in FIG. 1) to be received within and retained at the needle orifice 54, or the cannula may, alternatively, be adapted for connection to the syringe system 80 at the luer lock fitting 82 thereof.

It will be apparent that while a preferred embodiment of the invention has been shown and described, various modifications and changes may be made without departing from the true spirit and scope of the invention. For example, while the multiple injection systems of the present invention have been described as having particular application to facilitating the administration of an injection according to the SASH process, it is to be clearly understood that the syringe system may have other applications as well. That is to say, instead of filling the cartridges with saline and heparin to complete the SASH process, said cartridges can be filled with other fluids to complete any other medically accepted process. What is more, while the syringe systems of the present invention have been described as communicating with an IV catheter, it is also to be understood that the needle cannula may be used to penetrate the patient's tissue so that fluid may be delivered to the patient directly from the multiple injection syringe system without the need for an intermediate catheter, or the like.

Having thus set forth a preferred embodiment of the invention, what is claimed is:

1. A multiple injection syringe system, comprising:
   a hypodermic needle cannula having proximal and distal ends;
   cartridge carrier means in which a plurality of fluid filled cartridges are loaded, said cartridge carrier means having a space therein for receipt of said needle cannula;
   a manifold coupled to said cartridge carrier means, said needle cannula releasably retained by said manifold such that the distal end of cannula projects from said manifold in spaced alignment with the cartridges of said cartridge carrier means, said manifold being rotated relative to said cartridge carrier means to cause a corresponding displacement of said cannula;
   means for moving said cannula towards and away from said cartridge carrier means, said cannula moved towards said carrier means such that the proximal end of said cannula is placed into fluid communication with a selected cartridge from the plurality of cartridges in said cartridge carrier means, and said cannula moved away from said carrier means and out of fluid communication with the selected cartridge;
   means coupled to said cartridge carrier means for expulsing the fluid contents of the selected cartridge so that an injection may be administered by way of the distal end of said cannula when said cannula is in fluid communication with said cartridge; and
   needle releasing means carried by said manifold to release the needle cannula from said manifold and to position said cannula to be received within and shielded by said cartridge carrier means at the space therein after the injection has been administered and said cannula has been moved out of fluid communication with the selected cartridge.

2. The syringe system recited in claim 1, wherein said manifold is spaced from and movable towards and away from said cartridge carrier means for correspondingly moving said needle cannula towards said cartridge carrier means and placing the proximal end of said cannula into fluid communication with the selected cartridge of said carrier means and for moving said needle cannula away from said cartridge carrier means and out of fluid communication with the selected cartridge.

3. The syringe system recited in claim 1, further comprising a peripheral channel extending around said cartridge carrier means, said manifold including first rotation control means projecting therefrom to be received within and ride through said peripheral channel when said manifold is rotated in a first direction relative to said cartridge carrier means.

4. The syringe system recited in claim 3, further comprising stop means located within the peripheral channel of said cartridge carrier means, said stop means permitting said first rotation control means to ride through said peripheral channel when said manifold is rotated in said first direction relative to said cartridge carrier means and blocking said rotation control means from riding through said peripheral channel if said manifold is rotated in an opposite direction.

5. The syringe system recited in claim 4, further comprising at least one pair of axial channels formed at said cartridge carrier means and communicating with said peripheral channel thereof, and second rotation control means projecting from said manifold, said first rotation control means received in and advanced longitudinally through a first of said pair of axial channels and said second rotation control means received in and advanced longitudinally through the second of said pair of axial channels when said manifold is moved toward said cartridge carrier means for correspondingly moving the proximal end of said needle cannula into fluid communication with the selected cartridge, the receipt of said second rotation control means in said second axial channel preventing said manifold from rotating in said first direction.

6. The syringe system recited in claim 5, further comprising means to releasably secure said second rotation control means at its longitudinally advanced position within said second axial channel so as to lock said needle cannula in fluid communication with the selected cartridge.

7. The syringe system recited in claim 6, further comprising means by which to remove said second rotation control means from said second axial channel to permit said needle cannula to be moved out of communication with the selected cartridge and said manifold to rotate in the first direction relative to said cartridge carrier means.

8. The syringe system recited in claim 1, further comprising an orifice formed in said manifold and having a needle retaining portion in which to retain said needle cannula, said orifice having a needle releasing portion from which said cannula may be removed, said needle releasing means repositioning said cannula through said orifice from said needle retaining portion to said needle releasing portion.

9. The syringe system recited in claim 8, wherein said needle releasing means includes slide plate means movable laterally through said manifold and into contact with said needle cannula to displace said cannula through said orifice from said needle retaining portion to said needle releasing portion at which said cannula is released from said orifice.

10. The syringe system recited in claim 1, wherein said means for expulsing fluid from the selected cartridge is a fluid filled cylinder and a piston movable through said cylinder for generating a hydraulic force, said cylinder being connected in fluid communication with said cartridge carrier means so that the hydraulic force generated by said cylinder will cause the piston of the selected cartridge to be driven through said cartridge for expulsing the fluid therefrom via said needle cannula.

11. A syringe system having a longitudinally extending axis and comprising:
   a needle cannula;
   a cartridge carrier within which a plurality of fluid filled cartridges are located;
   a manifold coupled to said cartridge carrier and spaced axially from the cartridges located therewithin, said needle cannula retained by and projecting from said manifold such that said cannula is spaced from said cartridges when said manifold is coupled to said cartridge carrier, said manifold being rotated relative to said cartridge carrier to cause a corresponding displacement of said cannula;
   means by which to move said manifold axially towards and away from said cartridges, said manifold moved towards said cartridges to cause a corresponding axial movement of said needle cannula towards and into fluid communication with a selected one of said cartridges in said carrier, and said manifold moved away from said cartridges to move said needle cannula away from and out of fluid communication with said cartridge;
   a cylinder connected to said cartridge carrier and communicating with the cartridges therewithin; and
   a piston carried on a piston stem and movable through said cylinder for exerting a pressure on said cartridges and thereby causing the fluid within the selected cartridge to be expulsed via said cannula when said cannula is in fluid communication therewith.

12. The syringe system recited in claim 11, wherein said cylinder is filled with a fluid and fluidically coupled to the cartridges of said cartridge carrier, the movement of said piston through said cylinder exerting a hydraulic pressure on said cartridges for causing the fluid within the selected cartridge to be expulsed via said cannula.

13. The syringe system recited in claim 11, further comprising spring means extending between said manifold and the cartridges within said cartridge carrier and biased so as to oppose the movement of said manifold towards said cartridges, said manifold being moved against the bias of said spring means towards said cartridges so that said cannula is advanced therewith and moved into fluid communication with the selected one of said cartridges.

14. The syringe system recited in claim 11, further comprising at least one peripheral channel extending around said cartridge carrier; and
   rotation control means projecting from said manifold to be received in and ride through said channel when said manifold rotates relative to said carrier.

15. The syringe system recited in claim 14, further comprising a plurality of stops positioned within said peripheral channel of said cartridge carrier at locations corresponding to the locations of said plurality of cartridges within said carrier, said rotation control means being moved through said channel and into engagement with successive ones of said stops for causing said needle cannula projecting from said manifold to be axially aligned with and spaced from respective ones of said cartridges.

16. The syringe system recited in claim 15, wherein each of said plurality of stops is ramp shaped to permit said manifold to rotate in a first direction and said rotation control means to move in said first direction through said peripheral channel and over said ramp shaped stops, said stops blocking the counter rotation of said manifold and the movement of said rotation control means in an opposite direction through said peripheral channel.

17. The syringe system recited in claim 14, further comprising a plurality of longitudinally extending channels formed on said cartridge carrier and communicating with the peripheral channel thereof, said rotation control means moving through one of said longitudinal channels when said manifold is moved towards and away from said cartridges and said needle cannula is moved into and out of fluid communication with the selected one of said cartridges.

18. The syringe system recited in claim 17, wherein each of said plurality of longitudinal channels has a respective locking cavity located therein for receiving and releasably retaining said rotation control means to prevent the movement of said manifold away from said cartridges when said needle cannula has been moved into fluid communication with the selected one of said cartridges.

19. The syringe recited in claim 18, further comprising a finger ledge located on said manifold and being manually operable to cause a radially outward force to be exerted on said manifold so that said rotation control means is lifted out of receipt by the locking cavity in said longitudinal channel.

20. The syringe system recited in claim 11, further comprising means to release said needle cannula from said manifold so that said cannula is received within and shielded by said cartridge carrier at a space between the cartridges located therein.

21. The syringe system recited in claim 20, wherein said means to release said needle cannula from said manifold is a slide plate carried by said manifold and movable laterally therethrough into contact with said cannula.

22. The syringe recited in claim 21, wherein said manifold includes an orifice in which to receive and retain said needle cannula, said orifice having a needle retaining portion at which to retain said cannula and a needle releasing portion to which said cannula is moved when said slide plate is moved into contact therewith for releasing said cannula for receipt by said cartridge carrier.

23. A syringe system having a longitudinally extending axis and comprising:

a double ended needle cannula;

a cartridge carrier within which a plurality of fluid filled cartridges are located;

a manifold coupled to said cartridge carrier, said needle cannula retained by and projecting from said manifold such that a first end of said cannula is spaced from said cartridges, said manifold being rotated relative to said cartridge carrier to cause a corresponding displacement of said cannula;

means by which to move said cannula towards a selected one of said cartridges in said carrier to position the first end of said cannula in fluid communication with said cartridge;

a fluid filled cylinder coupled to said cartridge carrier;

fluid passage means extending between said fluid filled cylinder and respective ones of said cartridges within said cartridge carrier; and a piston movable through said cylinder for generating a hydraulic pressure, said hydraulic pressure being transmitted to said cartridges by way of said fluid passage means for causing the fluid within said selected cartridge to be expulsed therefrom and an injection administered via the second end of said cannula.

* * * * *